United States Patent
Merchant et al.

(10) Patent No.: US 9,732,387 B2
(45) Date of Patent: Aug. 15, 2017

(54) BIOMARKER ASSOCIATED WITH IRRITABLE BOWEL SYNDROME AND CROHN'S DISEASE

(71) Applicant: THE REGENTS OF THE UNIVERSITY OF MICHIGAN, Ann Arbor, MI (US)

(72) Inventors: Juanita L. Merchant, Ann Arbor, MI (US); Helmut Grasberger, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/389,961

(22) PCT Filed: Apr. 3, 2013

(86) PCT No.: PCT/US2013/035138
§ 371 (c)(1),
(2) Date: Dec. 8, 2014

(87) PCT Pub. No.: WO2013/152114
PCT Pub. Date: Oct. 10, 2013

(65) Prior Publication Data
US 2015/0065530 A1    Mar. 5, 2015

Related U.S. Application Data

(60) Provisional application No. 61/619,753, filed on Apr. 3, 2012.

(51) Int. Cl.
*C12Q 1/68* (2006.01)
*G06F 19/00* (2011.01)

(52) U.S. Cl.
CPC ........ *C12Q 1/6883* (2013.01); *G06F 19/3431* (2013.01); *G06F 19/3456* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,130,238 A | 7/1992 | Malek et al. |
| 5,270,184 A | 12/1993 | Walker et al. |
| 5,283,174 A | 2/1994 | Arnold, Jr. et al. |
| 5,399,491 A | 3/1995 | Kacian et al. |
| 5,455,166 A | 10/1995 | Walker |
| 5,480,784 A | 1/1996 | Kacian et al. |
| 5,695,934 A | 12/1997 | Brenner |
| 5,710,029 A | 1/1998 | Ryder et al. |
| 5,714,330 A | 2/1998 | Brenner et al. |
| 5,750,341 A | 5/1998 | Macevicz |
| 5,814,447 A | 9/1998 | Ishiguro et al. |
| 5,824,518 A | 10/1998 | Kacian et al. |
| 5,912,148 A | 6/1999 | Eggerding |
| 5,925,517 A | 7/1999 | Tyagi et al. |
| 5,928,862 A | 7/1999 | Morrison |
| 6,130,073 A | 10/2000 | Eggerding |
| 6,150,097 A | 11/2000 | Tyagi et al. |
| 6,210,891 B1 | 4/2001 | Nyren et al. |
| 6,258,568 B1 | 7/2001 | Nyren |
| 6,303,305 B1 | 10/2001 | Wittwer et al. |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,108,974 B2 | 9/2006 | Ecker et al. |
| 7,115,400 B1 | 10/2006 | Adessi et al. |
| 7,169,560 B2 | 1/2007 | Lapidus et al. |
| 7,282,337 B1 | 10/2007 | Harris |

(Continued)

FOREIGN PATENT DOCUMENTS

| | | |
|---|---|---|
| EP | 0684315 A1 | 11/1995 |
| WO | WO-0018957 A1 | 4/2000 |
| WO | WO-2006084132 A2 | 8/2006 |

OTHER PUBLICATIONS

Sun et al. 2005 vol. 29 p. 1.*
Langdahl (Journal of Bone and Mineral Research 2000 vol. 15 p. 402).*
Wall (Nature Reviews Genetics 2003 vol. 4, pp. 587-597).*
Juppner (Bone 1995 vol. 17 No. 2 Supplement 39S-42S).*
Lai et al. (BMC Medical Genetics 2005 VOl 6 p. 1-10).*
Camilleri et al. (Neurogasteoenterol Motil 2011 vol. 23 p. 193).*

(Continued)

*Primary Examiner* — Katherine Salmon

(74) *Attorney, Agent, or Firm* — Marshall, Gerstein & Borun LLP

(57) ABSTRACT

The present invention provides compositions and methods for characterizing irritable bowel syndrome. In particular, the present invention provides compositions and methods for determining polymorphisms associated with IBS-D and Crohn's disease. The present invention further provides compositions and methods for determining a treatment course of action in subjects with IBS-D and Crohn's disease.

6 Claims, 6 Drawing Sheets

(56) References Cited

U.S. PATENT DOCUMENTS

| | | |
|---|---|---|
| 7,329,492 B2 | 2/2008 | Hardin et al. |
| 7,482,120 B2 | 1/2009 | Buzby |
| 7,501,245 B2 | 3/2009 | Quake et al. |
| 7,668,697 B2 | 2/2010 | Volkov et al. |
| 8,017,322 B2 | 9/2011 | Ecker et al. |
| 8,017,743 B2 | 9/2011 | Ecker et al. |
| 2005/0042638 A1 | 2/2005 | Arnold et al. |
| 2005/0130173 A1 | 6/2005 | Leamon et al. |
| 2006/0046265 A1 | 3/2006 | Becker et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |

OTHER PUBLICATIONS

Adessi et al., Solid phase DNA amplification: characterisation of primer attachment and amplification mechanisms. *Nucleic Acid Res.*, 28(20):E87 (2000).

Astier et al., Toward single molecule DNA sequencing: direct identification of ribonucleoside and deoxyribonucleoside 5'-monophosphates by using an engineered protein nanopore equipped with a molecular adapter. *J Am Chem Soc.*, 128(5):1705-10 (2006).

Bennett et al., Toward the 1,000 dollars human genome. *Pharmacogenomics*, 6(4):373-382 (2005).

Birren et al., Genome Analysis: Analyzing DNA, A Laboratory 1, Cold Spring Harbor, N.Y. (1997).

Branton et al., The potential and challenges of nanopore sequencing. *Nat. Biotechnol.*, 26(10):1146-53 (2008).

Brenner et al., Gene expression analysis by massively parallel signature sequencing (MPSS) on microbead arrays. Accurate sequencing by hybridization for DNA diagnostics and individual genomics. *Nat. Biotechnol.*, 18 (6):630-634 (2000).

Camilleri et al., LX-1031, a tryptophan 5-hydroxylase inhibitor, and its potential in chronic diarrhea associated with increased serotonin, *Neurogastroenterol Motil.* 23(3):193-200 (2011).

Cheung et al., Integration of cytogenetic landmarks into the draft sequence of the human genome. *Nature*, 409(6822):953-958 (2001).

Drmanac, et al., Accurate sequencing by hybridization for DNA diagnostics and individual genomics. *Nat. Biotechnol.*, 16:54-58 (1998).

Eid et al., Real-time DNA sequencing from single polymerase molecules. *Science*, 323 (1510):133-138 (2009).

Guatelli et al., Isothermal, in vitro amplification of nucleic acids by a multienzyme reaction modeled after retroviral replication. *Proc. Natl. Acad. Sci. USA*, 87(5):1874 (1990).

Harris et al., Single-molecule DNA sequencing of a viral genome. *Science*, 320(5872):106-109 (2008).

Helmut et al., A Functional Promoter Variant in the Tryptophan Hydroxylase 1 Gene is Associated With a Bowel Habit Phenotype in Patients With Irritable Bowel Syndrome (IBS), *Gastroenterology*, 140(5)1:S111 (2011).

Helmut et al., EGR-1 Binds a Common Proximal Promoter SNP and Mediates Allele-Specific Differences in TPH1 Promoter Activity, *Gastroenterology*, 140(5)1:S630-S631 (2011).

Jun et al., Associations of tryptophan hydroxylase gene polymorphisms with irritable bowel syndrome, *Neurogastroenterol Motil.* 23(3):233-9, e116 (2011).

Kato, Impact of the next generation DNA sequencers. *Int. J. Clin. Exp. Med.*, 2(2):193-202 (2009).

Korlach et al., Selective aluminum passivation for targeted immobilization of single DNA polymerase molecules in zero-mode waveguide nanostructures. *Proc. Natl. Acad. Sci. USA* 105(4):1176-1181 (2008).

Kwoh et al., Transcription-based amplification system and detection of amplified human immunodeficiency virus type 1 with a bead-based sandwich hybridization format. *Proc. Natl. Acad. Sci. USA*, 86(4):1173 (1989).

Levene et al., Zero-mode waveguides for single-molecule analysis at high concentrations. *Science*, 299(5607):682-686 (2003).

Lizardi et al., Exponential Amplification of Recombinant-RNA Hybridization Probes. *BioTechnol.* 6:1197-1202 (1988).

MacLean et al., Application of 'next-generation' sequencing technologies to microbial genetics. Nature Rev. *Microbiol.*, 7: 287-296 (2009).

Margulies et al., Genome sequencing in microfabricated high-density picolitre reactors. *Nature* 437(7057):376-380 (2005).

Maxam and Gilbert, A new method for sequencing DNA. *Proc. Natl. Acad. Sci. USA* 74:560-564 (1977).

Merchant et al., ZBP-89, Serotonin and IBS: Lessons Learned from Bridging the Translational Divide, CURE Digestive Diseases Research Center: 2012 Annual Research Meeting, Mar. 16, 2012.

Minderhoud et al., Serotonin Synthesis and Uptake in Symptomatic Patients With Crohn's; Disease in Remission. *Clin Gastroenterol Hepatol.* 5(6):714-20 (2007).

Mitra et al., Fluorescent in situ sequencing on polymerase colonies. *Analytical Biochemistry* 320(1):55-65 (2003).

Morozova and Marra, Applications of next-generation sequencing technologies in functional genomics. *Genomics*, 92(5):255 (2008).

Mullis et al., Specific synthesis of DNA in vitro via a polymerase-catalyzed chain reaction. *Meth. Enzymol.* 155: 335-50 (1987).

Murakawa et al., Direct detection of HIV-1 RNA from AIDS and ARC patient samples, *DNA*, 7(4): 287 (1988).

Norman C. Nelson et al., Nonisotopic Probing, Blotting, and Sequencing, ch. 17 (Larry J. Kricka ed., 2d ed. (1995).

Pennisi E. Genomics. Semiconductors inspire new sequencing technologies. *Science*, 327(5970): 1190 (2010).

Persing, David H., "In Vitro Nucleic Acid Amplification Techniques" in Diagnostic Medical Microbiology: Principles and Applications (Persing et al., Eds.), pp. 51-87 (American Society for Microbiology, Washington, DC (1993).

Ravic et al., S1204 Serotonin Transporter Gene Polymorphisms in Crohn's Disease Patients. Polymorphisms in Patients with Crohn's Colitis and Ulcerative Colitis, *Gastroenterology*, 136(5):A-212 (2009).

Ronaghi et al., Real-time DNA sequencing using detection of pyrophosphate release. *Anal. Biochem.*, 242(1):84-89 (1996).

Ruparel et al., Design and synthesis of a 3'-O-allyl photocleavable fluorescent nucleotide as a reversible terminator for DNA sequencing by synthesis. *Proc. Natl. Acad. Sci. USA* 102(17):5932-5937 (2005).

Saito, The Role of Genetics in IBS, *Gastroenterol Clin North Am.*, 40(1):45-67 (2011).

Sanger et al., DNA sequencing with chain-terminating inhibitors. *Proc. Natl. Acad. Sci. USA* 74(12):5463-5467 (1997).

Shendure et al., Accurate multiplex polony sequencing of an evolved bacterial genome. *Science*, 309(5741), 1728-1732 (2005).

Sun et al., A functional polymorphism in the promoter region of the tryptophan hydroxylase gene is associated with alcohol dependence in one aboriginal group in Taiwan, *Alcohol Clin Exp Res.*, 29(1):1-7 (2005).

Voelkerding et al., Next-generation sequencing: from basic research to diagnostics. *Clinical Chem.*, 55(4):641-58, (2009).

Walker et al., Isothermal in vitro amplification of DNA by a restriction enzyme/DNA polymerase system. *Proc. Nail. Acad. Sci. USA* 89(1): 392-396 (1992).

Weiss R., Hot prospect for new gene amplifier, *Science*, 254(5036): 1292 (1991).

International Search Report and Written Opinion of the International Searching Authority, European Patent Office, PCT/US2013/035138, dated Mar. 6, 2013.

International Preliminary Report on Patentability, PCT/US2013/035138, European Patent Office, dated Oct. 7, 2014.

\* cited by examiner

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
ctgcgtgtat ctgactggtg t                                         21

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
gggataagga gctaatcgac tga                                       23

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gaaaggtctc tccctgacca                                           20

<210> SEQ ID NO 4
<211> LENGTH: 36
<212> TYPE: DNA
<213> ORGANISM: Artificial Sequence
<220> FEATURE:
<223> OTHER INFORMATION: Synthetic primer
```

```
<400> SEQUENCE: 4
cagaagcaca gagakgtgtg ggaggtgggg ggattc                          36

<210> SEQ ID NO 5
<211> LENGTH: 31
<212> TYPE: DNA
<213> ORGANISM: Artificial Sequence
<220> FEATURE:
<223> OTHER INFORMATION: Synthetic primer

<400> SEQUENCE: 5
tatggtacct ttgggataag gagctaatcg a                               31

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
tatctcgagt aggtgcaggc tgggtcg                                    27
```

BIOMARKER ASSOCIATED WITH IRRITABLE BOWEL SYNDROME AND CROHN'S DISEASE

CROSS REFERENCE TO RELATED APPLICATIONS

This application is a U.S. national phase application under 35 U.S.C. §371 of International Application No. PCT/US2013/035138, filed on Apr. 3, 2013, entitled "Biomarker Associated with Irritable Bowel Syndrome and Crohn's Disease," which claims the priority of U.S. Patent Application No. 61/619,753 filed Apr. 3, 2012, the entire respective disclosures of which are incorporated herein by reference.

This invention was made with government support under DK055732 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form (filename: 46907A_SeqListing.txt; created 1 Oct. 2014, 1,449 byte—ASCII text file) which is incorporated by reference in its entirety.

FIELD OF INVENTION

The present invention provides compositions and methods for characterizing irritable bowel syndrome. In particular, the present invention provides compositions and methods for determining polymorphisms associated with IBS-D and Crohn's disease. The present invention further provides compositions and methods for determining a treatment course of action in subjects with IBS-D and Crohn's disease.

BACKGROUND

Abnormalities in serotonin (5-HT) signaling have been implicated in IBS pathogenesis. When induced by luminal chemical and mechanical signals, enterochromaffin (EC) cells release 5-HT, which stimulates 5-HT3 and 5-HT4 receptors on primary afferent neurons, which feed into peristaltic and secretomotor reflexes, regulating intestinal motility and secretion.[1] In patients with diarrhea-predominant IBS (IBS-D), platelet-depleted postprandial plasma 5-HT concentrations are higher compared to patients with constipation (IBS-C) and healthy controls,[2-5] while IBS-C patients have a mitigated postprandial rise in plasma 5-HT compared to controls.[3,6] Plasma 5-HT is almost exclusively derived from gut EC cells secreting 5-HT, which is not taken up by platelets and overflows into the circulation.[1] Plasma 5-HT levels also positively correlate with gut motility under both fasting and fed conditions[7] suggesting that they parallel the mucosal bioavailability of 5-HT in the intestine. Together, these findings suggest that differences in mucosal 5-HT levels are involved in the clinical bowel habit phenotype in IBS. This concept is indirectly supported by the beneficial effects of 5-HT4 receptor agonists in IBS-C and 5-HT3 antagonists in IBS-D.[8]

One factor that could modulate mucosal 5-HT availability is the activity or expression of the 5-HT selective reuptake transporter (SERT), which terminates hormone action and prevents receptor desensitization by removing it from the interstitial space. While SERT mRNA is widely expressed, the quantities found in the gut epithelium are very low, particularly in the colon. It may thus not be surprising that conflicting results have been reported concerning colonic SERT mRNA in IBS.[9-12]

Conceivably, 5-HT biosynthesis is another process potentially influencing mucosal signaling. Tryptophan hydroxylase-1 (TPH1) is the rate-limiting enzyme in the biosynthesis of 5-HT in EC and mast cells. Both TPH1 and TPH2 are expressed in the gut, but TPH2 is expressed by enteric and central neurons, while TPH1 is the predominant enzyme in EC cells.[13] Although the activity of TPH1 is controlled at multiple levels including posttranslational regulation,[14] recent evidence from animal studies indicates that changes in TPH1 transcription can affect proportional changes in intestinal and plasma 5-HT levels.[15] TPH1 is therefore an intriguing candidate gene for conditions with altered 5-HT bioavailability as proposed for the distinct bowel habit subtypes in IBS.

This idea is the basis for the development of an oral TPH inhibitor acting locally on the GI mucosa.[15] A recent phase II clinical trial demonstrated the efficacy of this novel compound in relieving symptoms of non-constipating IBS.[16-18] The clinical response to therapy correlated with a decrease in 24-h urine excretion of the metabolite 5-hydroxyindoleacetic acid reflecting reduced 5-HT biosynthesis, which is promising particularly since there is currently a lack of established biomarkers to predict treatment response in IBS.

SUMMARY OF THE INVENTION

The present invention provides compositions and methods for characterizing irritable bowel syndrome. In particular, the present invention provides compositions and methods for determining polymorphisms associated with IBS-D and Crohn's disease. The present invention further provides compositions and methods for determining a treatment course of action in subjects with IBS-D and Crohn's disease.

For example, in some embodiments, the present invention provides methods comprising: a) analyzing a sample from a subject with a nucleic acid detection assay to determine that the subject has a −347 C/A polymorphism in the promoter of the TPH1 gene, and/or a SNP in linkage disequilibrium with the −347 C/A polymorphism, thereby generating a tryptophan hydroxylase 1 (TPH1) genetic analysis result; and b) processing the TPH1 genetic analysis result to determine if the subject has a polymorphism indicative of irritable bowel syndrome (IBS) or has Crohn's disease.

In particular embodiments, the IBS is IBS-diarrhea (IBS-D). In other embodiments, it is determined that the subject has the −347 C polymorphism. In some embodiments, the SNP in linkage disequilibrium is −1066T/C. In other embodiments, the −347C polymorphism is indicative of IBS-D, and the −347A polymorphism is indicative of Crohn's disease in the subject. In particular embodiments, the methods further comprise the step of determining the presence of one or more polymorphisms selected from the group consisting of rs10444225, rs10766452, rs10766453, rs1079785, rs11024462, rs11024465, rs12361971, rs2403246, rs4757610, rs4757611, rs6486403, rs7106970, rs7110238, rs7122118, rs7130929, rs7936469, rs7937368, rs7939791, rs7943526, rs7944348, rs7950705, and rs7950928 in the subject. In certain embodiments, the processing is processed with a computer system. In other embodiments, the subject is of Caucasian and/or Asian ancestry.

In other embodiments, the present invention provides methods comprising: a) analyzing a sample from a subject with a SNP detection assay to determine that the subject has a −347 C/A polymorphism in the promoter of the TPH1 gene, and/or a SNP in linkage disequilibrium with the −347 C/A polymorphism, thereby generating a TPH1 genetic analysis result; and b) processing the TPH1 genetic analysis result with a computer system to generate an outcome that indicates that the subject should receive a serotonin antagonist medication.

In further embodiments, the serotonin antagonist medication targets TPH. In other embodiments, the medication is LX1031. In some embodiments, it is determined that the subject has the −347C polymorphism. In additional embodiments, it is determined that the subject has the −1066T polymorphism. In further embodiments, the −347C polymorphism is indicative of IBS-D, and the −347A polymorphism is indicative of Crohn's disease in the subject.

In some embodiments, the present invention provides method of treating a subject identified as having a −347 C polymorphism in the promoter of the TPH1 gene, and/or a SNP in linkage disequilibrium with the −347 C polymorphism, comprising: administering to the subject a serotonin antagonist medication. In particular embodiments, the serotonin antagonist medication targets TPH. In other embodiments, the medication is LX1031.

In certain embodiments, the present invention provides methods comprising: a) analyzing a sample from a subject with a nucleic acid detection assay to determine that the subject has a −347 C/A polymorphism in the promoter of the TPH1 gene, and/or a SNP in linkage disequilibrium with the −347 C/A polymorphism; and b) administering to the subject a serotonin antagonist medication.

In further embodiments, the present invention provides kits or systems comprising: a) a serotonin antagonist medication, and b) a nucleic acid detection assay to determine that a subject has a −347 C/A polymorphism in the promoter of the TPH1 gene, and/or a SNP in linkage disequilibrium with the −347 C/A polymorphism.

In particular embodiments, the present invention provides methods comprising: a) analyzing a sample from a subject with a nucleic acid detection assay to determine that the subject has a −347A polymorphism in the promoter of the TPH1 gene, and/or a SNP in linkage disequilibrium with the −347A polymorphism; and b) identifying the subject as having Crohn's disease and/or informing the patient or the patient's doctor that the subject has Crohn's disease and/or administering a Crohn's disease treating medication to the subject.

In other embodiments, the present invention provides methods comprising: a) analyzing a sample from a subject with a nucleic acid detection assay to determine that the subject has a −347C polymorphism in the promoter of the TPH1 gene, and/or a SNP in linkage disequilibrium with the −347C polymorphism; and b) identifying the subject as having IBS-D and/or informing the patient or the patient's doctor that the subject has IBS-D.

DEFINITIONS

Figure 1:
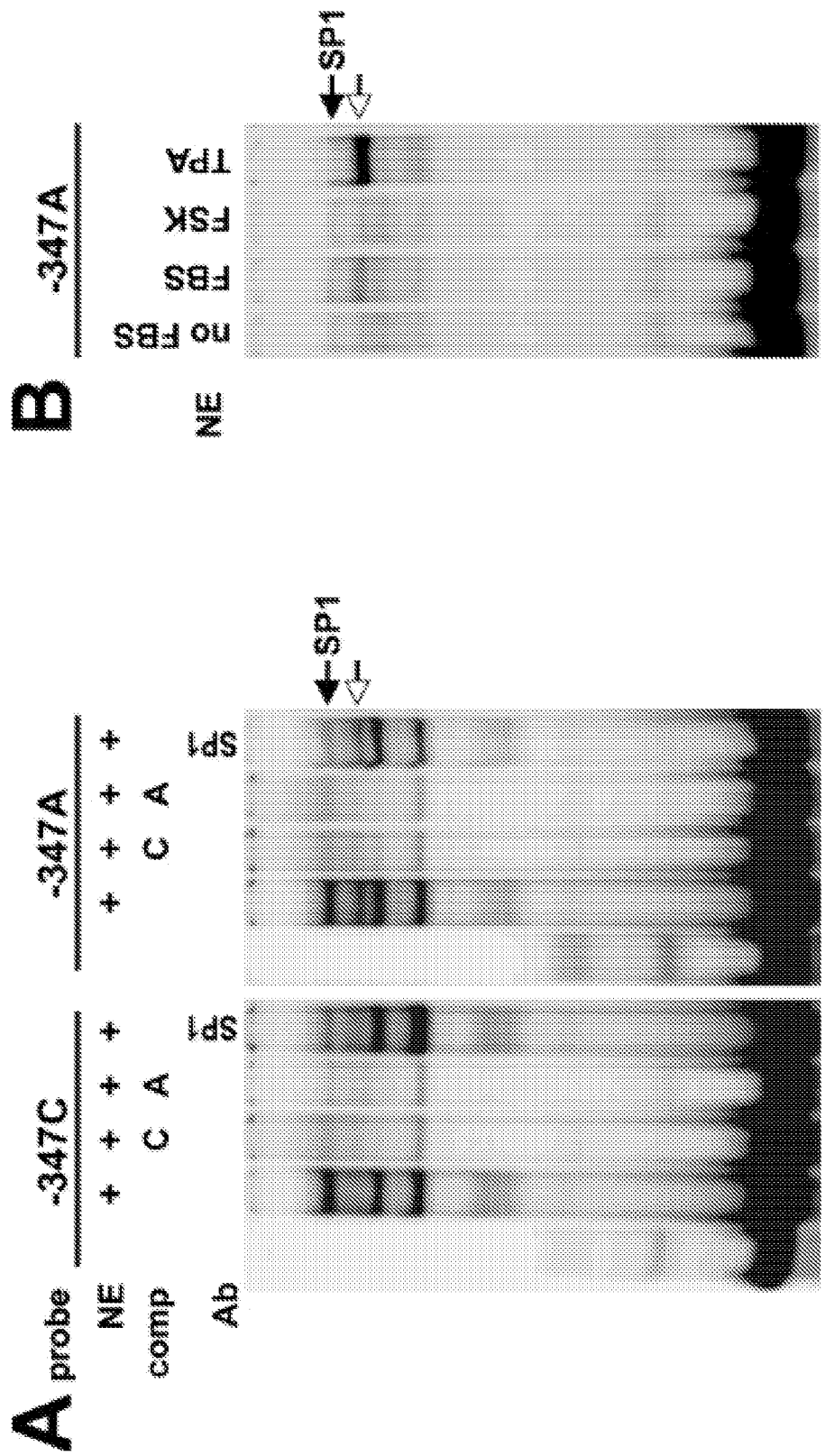
FIG. 1. Allele-specific binding of EGR-1 to the −347C/A polymorphism of the TPH1 core promoter. (A) Electrophoretic mobility shift assay using allele-specific probes (−347C and −347A) and nuclear protein extract (NE) prepared from BON cells. The open arrow marks the position of a protein complex with preferential binding to the −347A-allele. Specific competition (comp) was performed by co-incubation with 100-fold molar excess of cold probes. (B) Expression of the −347A-allele specific binding activity in serum starved BON cells (no FBS) treated for one hour with 20% fetal bovine serum (FBS), PKC-activating phorbol ester (TPA), or the adenylyl cyclase activator forskolin (FSK). (C) Supershift experiments to determine the TPA-induced (200 nM; 1 h) nuclear factor with preferential binding to the −347A-allele. (D) Western blot analysis of EGR-1 expression in BON cells treated with FBS or TPA. The kinetics of EGR-1 expression is compatible with the induction of the nuclear factor binding preferentially to the A-allele. (E) Location of SNP −347C/A at position −1 relative to a consensus nonameric EGR recognition motif. The −347A-allele corresponds to the preferred nucleotide according to the extended EGR binding matrix determined by in vitro DNA binding site selection (depicted as sequence logo).[25,42]
Figure 1:
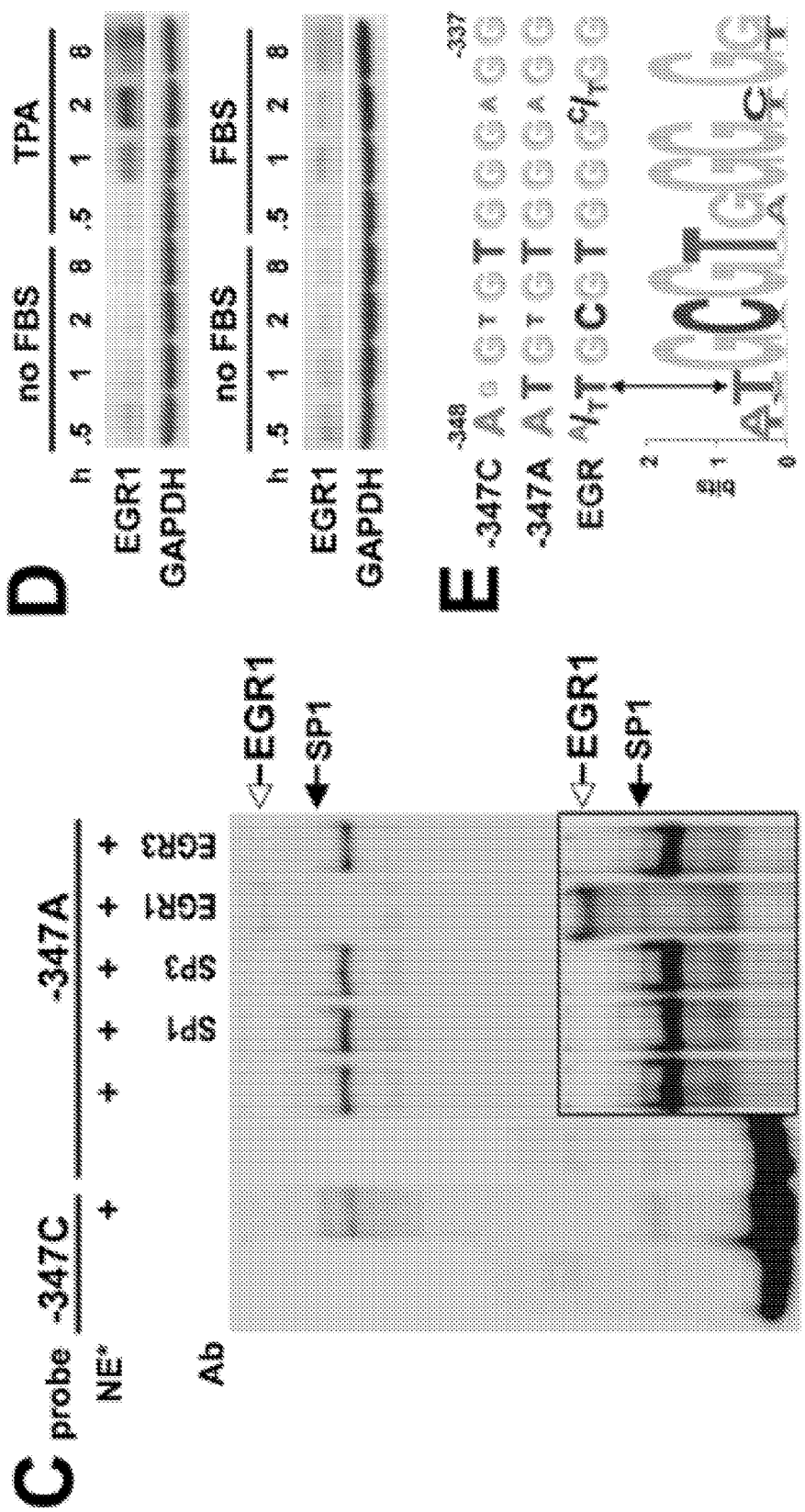

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., murines, simians, equines, bovines, porcines, canines, felines, and the like), and most preferably includes humans.

The term "diagnosed," as used herein, refers to the recognition of a disease by its signs and symptoms, or genetic analysis, pathological analysis, histological analysis, and the like.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION

The present invention provides compositions and methods for characterizing irritable bowel syndrome. In particular, the present invention provides compositions and methods for determining polymorphisms associated with IBS-D (diarrhea associated with IBS). The present invention further provides compositions and methods for determining a treatment course of action in subjects with IBS-D.

Alterations in 5-hydroxytryptamine (5-HT) signaling have been implicated in altered bowel habits in irritable bowel syndrome (IBS). Tryptophan hydroxylase 1 (TPH1) is the rate-limiting enzyme for 5-HT synthesis in enterochromaffin cells. Work conducted during development of embodiments of the present invention sought to assess the function of the only common TPH1 proximal promoter variant (−347C/A; rs7130929) and its association with bowel habit predominance and colonic TPH1 expression in IBS. As described in the Example below, the following methods were used. Electrophoretic mobility shift assays and luciferase reporter assays were performed to assess the function of −347C/A in vitro. Genotype distribution was determined for 219 IBS patients subtyped using Rome III criteria and 312 healthy controls. Association with bowel habit was tested using a multinomial logistic regression model controlling for race and anxiety. Colonic mucosal TPH1 mRNA expression was measured in a subset of subjects (62 IBS patients and 50 controls). The Examples shows that early growth response factor 1 (EGR1) bound to an allele-specific site comprising SNP −347C/A and modulated TPH1 promoter activity. There was a greater prevalence of the CC genotype in the IBS-D subtype (56%) compared to the IBS-C (31%) and IBS-M (38%) subtypes (P=0.05) as well as normal controls (42%). Colonic mucosal expression of TPH1 tended to be higher in IBS-diarrhea (IBS-D) versus IBS-constipation (IBS-C) and in IBS patients who were homozygous for the C-allele. This word demonstrated a functional TPH1 promoter SNP −347C/A is associated with IBS bowel habit subtypes and colonic TPH1 expression consistent with a role of TPH1 in modulating intestinal 5-HT signaling.

I. Diagnostic and Screening Methods

In some embodiments, the present invention provides compositions and method for screening for or diagnosing IBS, in particular IBS-D. For example, in some embodiments, the present invention provides compositions and methods for identifying polymorphisms in the TPH1 gene associated with IBS-D.

The present invention is not limited to a particular TPH1 polymorphism. For example, in some embodiments, polymorphisms in the promoter of TPH1 are analyzed. Examples include, but are not limited to, a C at −347 C/A (rs7130929), or the corresponding G in the opposite strand, and a T at −1066T/C; (rs4537731), or the corresponding A in the opposite strand. Additional polymorphisms useful in embodiments of the present invention include, but are not limited to, SNPs in linkage disequilibrium with −347 C/A, and rs10444225, rs10766452, rs10766453, rs1079785, rs11024462, rs11024465, rs12361971, rs2403246, rs4537731, rs4757610, rs4757611, rs6486403, rs7106970, rs7110238, rs7122118, rs7130929, rs7936469, rs7937368, rs7939791, rs7943526, rs7944348, rs7950705, or rs7950928.

The presence of a given polymorphism may be determined using any suitable method. Exemplary analysis methods are described below.

A. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four flours at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing (see, e.g., Astier et al., J. Am. Chem. Soc. 2006 Feb. 8; 128(5):1705-10, herein incorporated by reference) is utilized. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the HeliScope by Helicos Bio-Sciences technology is utilized (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

In some embodiments, the nucleic acid sequencing approach developed by Stratos Genomics, Inc. and involves the use of Xpandomers is utilized. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

B. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., TPH1) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, polymorphisms are detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

C. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., TPH1) by comparing gene expression or mutation status in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

D. Amplification

Nucleic acids (e.g., TPH1) may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

E. Detection Methods

Non-amplified or amplified nucleic acids can be detected by any conventional means. For example, the TPH1 polymorphisms can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, nucleic acids are detected and characterized by the identification of a unique base composition signature (BCS) using mass spectrometry (e.g., Abbott PLEX-ID system, Abbot Ibis Biosciences, Abbott Park, Ill.,) described in U.S. Pat. Nos. 7,108,974, 8,017,743, and 8,017,322; each of which is herein incorporated by reference in its entirety.

F. Data Analysis

In some embodiments, a computer-based analysis program is used to translate the raw data generated by the detection assay (e.g., the presence, absence, or amount of a polymorphism) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a cheek swab sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a TPH1 polymorphism) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

G. Compositions & Kits

Compositions for use in the diagnostic methods described herein include, but are not limited to, probes, amplification oligonucleotides, and the like. The probe and antibody compositions may also be provided in the form of an array.

II. Companion Diagnostic Applications

In some embodiments, the present invention provides compositions and methods for determining a treatment course of action. For example, in some embodiments, an individual's TPH1 polymorphism status is determined (e.g., using the methods described above). In some embodiments, subjects found to have a polymorphism indicative of IBS-D (e.g., one or more of the polymorphisms described herein) are administered a serotonin antagonist medication. In some embodiments, the serotonin antagonist medication targets TPH. TPH targeting drugs are known in the art. Examples include, but are not limited to, LX1031 (available from, for example, Lexicon Pharmaceuticals, Woodlands, Tex.).

EXAMPLES

Example 1

Identification of IBS-D Associated SNP

This Example describes the identification of the −347 A/C SNP as associated with chronic diarrhea in Irritable Bowel Syndrome patients.

Methods

Human Study Subjects

Male and female IBS patients and healthy control subjects who were at least 18 years of age and participating in clinical research studies at the Oppenheimer Family Center for Neurobiology of Stress at UCLA were consecutively recruited to provide saliva for DNA analysis. For the colonic biopsy study, IBS patients and healthy controls between the ages of 18 and 55 were recruited, although subjects were not consecutively enrolled. The diagnosis of IBS and bowel habit subtyping was determined by Rome III criteria,[19] the absence of other chronic gastrointestinal (GI) conditions that could explain IBS symptoms, and by a clinician with expertise in IBS. Healthy control subjects were recruited by advertisement and did not have a history of IBS or other chronic GI or pain conditions, and were not taking psychotropic medication or participating in psychotherapy. Validated questionnaires were used to assess IBS symptoms. Depression and anxiety symptoms were measured using the Hospital Anxiety and Depression (HAD) scale.[20] Subjects were compensated for their participation in the study. The UCLA Institutional Review Board approved this study and informed consent was obtained from all subjects.

Genotyping

Saliva for DNA isolation was collected using the Oragene DNA Self-Collection Kit (DNA Genotek, Inc., Ottawa, Canada). DNA was extracted at the UCLA Biological Samples Processing Core. For genotyping of the −347C/A variant by restriction fragment length polymorphism (RFLP), a 484 bp fragment was amplified by hotstart PCR (Qiagen) with primers 5'-CTGCGTGTATCTGACTG-GTGT-3' (SEQ ID NO:1) and 5'-GGGA-TAAGGAGCTAATCGACTGA-3' (SEQ ID NO:2), digested with MslI restriction enzyme (New England Biolabs) and separated on 2% agarose gels. Only amplicons from the A-allele were cut into 207 bp and 277 bp fragments. RFLP fragments were confirmed by sequencing. A 1149 bp region of the human TPH1 promoter region was amplified using Platinum Taq DNA polymerase (Invitrogen) and oligonucleotide primers 5'-CTGCGTGTATCTGACTGGTGT-3' (SEQ ID NO:1) and 5'-GAAAGGTCTCTCCCTGACCA-3' (SEQ ID NO:3)[21] in subsets of the IBS and control populations. The amplified alleles were then sequenced bidirectionally at the UM DNA Sequencing Core. A perfect agreement between −347C/A genotypes by RFLP and DNA sequencing was found for all 436 samples analyzed by both methods.

Measurement of TPH1 Messenger RNA in Colonic Biopsies

A flexible sigmoidoscopy to at least 40 cm from the anal verge was performed in the UCLA Medical Procedures Unit. Subjects were instructed to use two tap-water enemas as the bowel preparation. During the sigmoidoscopy, sigmoid colon biopsies were taken at 30 cm from the anal verge.

For detection of TPH1 mRNA, 100 ng of RNA isolated from colonic biopsies were reverse-transcribed into cDNA using the Taqman One-step RT-PCR kit (Applied Biosystems, Foster City, Calif.) and incubated with dual fluorogenic probes (Applied Biosystems, Foster City, Calif.). 18S rRNA was used as an endogenous control and was detected using dual labeled fluorogenic probe (5'-FAM/3'-MGB probe, # Hs00188220, Applied Biosystems, Foster City, Calif.). mRNA levels for TPH1 were quantified using a fluorogenic 5'-nuclease PCR assay with a 7500 Fast Real-Time PCR sequence detection system (Applied Biosystems, Foster City, Calif.). Duplicate reactions of each standard or sample were denatured for 10 seconds at 95° C., and subjected to 40 cycles of denaturation at 95° C. for 3 seconds followed by annealing and extension at 60° C. for 30 seconds.

Cell Culture

BON cells, a human 5-HT producing pancreatic carcinoid cell line[22] were grown in DME/F-12 (1:1) supplemented with 2.5 mM L-glutamine, 15 mM Hepes, and 10% heat-inactivated fetal bovine serum (FBS). In stimulation experiments, cells were serum starved for 24 h, followed by incubation for 0.5 to 8 h with 20% FBS (20%), 20-200 nM 12-O-tetradecanoylphorbol-13-acetate (TPA), or 10 µM forskolin.

Electrophoretic Mobility Shift Assay (EMSA)

Nuclear protein extracts from BON cells were prepared essentially as described,[23] and protein concentrations determined by the bicinchoninic acid method (BCA assay; Pierce Biotechnology) with bovine serum albumin standard curves. The band shift probes were prepared by $^{32}$P-end labeling of two allele specific pairs of PAGE-purified complementary oligonucleotides corresponding to the −361/−326 region of the TPH1 promoter (5'-CAGAAGCACAGAGA(g/t)GT-GTGGGAGGTGGGGGGATTC-3'-SEQ ID NO:4) using T4 Polynucleotide Kinase. Duplex DNA assembled by annealing of the labeled complementary oligonucleotides was purified on G50 spin columns. The specific competitor double-stranded DNAs were prepared by annealing of the unlabeled oligonucleotides. Binding reactions contained 0.5 pmol probe, 2 µg nuclear protein extract, 0.5 µg sonicated salmon sperm DNA, and 0.5 µg poly(dI-dC) (Amersham Biosciences) in a total volume of 20 µl. All binding reactions were carried out in binding buffer consisting of 20 mM Hepes (pH 7.9), 5 mM $MgCl_2$, 50 mM KCl, 100 µM $ZnSO_4$, 0.5 mM dithiothreitol, and 10% glycerol. After incubation (10 min at room temperature followed by 20 min on ice), the samples were loaded onto a 5% polyacrylamide gel (acrylamide:bis-acrylamide 37.5:1) and separated at 10 V/cm in 0.5×TBE (45 mM Tris base, 45 mM boric acid, 1 mM EDTA). Dried gels were analyzed by autoradiography. For antibody interference, the reaction mixtures lacking the probe were incubated for 20 min on ice with antibodies against Sp1 (clone H225), Sp3 (D20), EGR-3 (C-24), EGR-1 (rabbit polyclonal 588), GATA-1 (N6; all from Santa Cruz Biotechnology, Inc.), or ZBP-89,[24] before addition of the probe and further processing as above. For competition experiments, unlabeled competitor DNAs in 100-fold molar excess over the labeled probe were included in the binding reactions.

Western Blotting

BON cells were homogenized in lysis buffer (50 mM Tris/HCl (pH 8.0), 150 mM NaCl, 0.1% sodium dodecyl sulfate, 0.5% sodium deoxycholate, 1% NP40) containing a protease inhibitor cocktail (Complete; Roche, Indianapolis, Ind.). Fifty micrograms protein/well was separated on 4-20% gradient SDS-polyacrylamide gels under reducing conditions and blotted to PVDF membranes. Blots were probed with anti-EGR-1 (S-25, Santa Cruz Biotechnology, Inc.) and anti-GAPDH (MAB374, Millipore).

Luciferase Reporter Assays

The −568/+19 promoter region of the human TPH1 gene was amplified using primers forward 5'-TATGGTAC-CTTTGGGATAAGGAGCTAATCGA-3' (SEQ ID NO:5) and reverse 5'-TATCTCGAGTAGGTGCAG-GCTGGGTCG-3' (SEQ ID NO:6) from genomic DNA of subjects homozygous for either the A- or C-allele of SNP rs7130929 (−347C/A). The two products were cloned directionally into the KpnI and XhoI restriction sites of the promoter-less luciferase reporter vector pGL3-basic (Promega) to generate −347A-Luc and −347C-Luc, respectively. Plasmids containing TPH1 promoter sequences were unstable when amplified in the DH5α *E. coli* strain and were therefore prepared in the *E. coli* Stbl2 strain (Invitrogen) grown at 30° C. Both constructs were confirmed by sequencing revealing a single nucleotide difference corresponding to the expected −347C/A SNP alleles.

One day before transfection, BON were seeded onto 24-well plates without antibiotics to obtain 90-95% confluence at the time of transfection. For each experiment, the cultured cells were transiently transfected in triplicate with 0.25 µg/well of the TPH1 reporter constructs using Lipofectamine 2000 transfection reagent (Invitrogen) diluted in serum-free OptiMEM I. Twenty ng/well of the pRL-Tk plasmid (Promega), expressing *Renilla* luciferase from a thymidine kinase promoter, was co-transfected as an internal control. The medium was replaced by fresh DME/F-12 8 h following transfection. To evaluate the effect of EGR-1 overexpression, cells were co-transfected with 0.2 µg/well of a human EGR-1 expression vector (Origene) or empty pCMV6 vector as the control, and luciferase activity was measured 24 hours post transfection. In EGR1 knockdown experiments, BON cells were co-transfected with either 20 pmol/well of EGR1 siRNA (Silencer Select s4538; Invitrogen) or scrambled control siRNA (control siRNA No. 2; Invitrogen). Twenty-four hours following transfection with siRNA, the cells were stimulated for 4 hours with 200 nM TPA before assaying for luciferase activity.

Statistical Analysis

Hardy-Weinberg equilibrium was tested for the TPH1 SNP. An additive effect genetic model was tested among IBS cases and controls using a Cochran-Armitage test for trend. A Fisher's exact test was used to compare TPH1 genotypes with Rome 3 bowel habit. Multinominal logistic regression was used to predict Rome 3 bowel habit from the TPH1 SNP controlling for race/ethnicity and HAD anxiety within the full set of samples and within Caucasians only. Adjusted odds ratios (OR) and corresponding 95% confidence intervals were reported from the models. TPH1 mRNA data was log-transformed to achieve approximate normality and geometric means and 95% CI were reported. A two-sample t-test was used to compare TPH1 mRNA expression between IBS cases and controls, ANOVA was used to compare TPH1 mRNA levels across bowel habit, and Spearman corelation was used to compare gene expression across additively coded TPH1 genotypes. All statistical analyses were performed using SAS version 9.2 (SAS Institute, Cary, N.C., USA) or R version 2.14.0. Significance was assessed at a 0.05 level.

Results

Allele-Specific Nuclear Protein Binding to the Proximal TPH1 Promoter Variant

Figure 5:
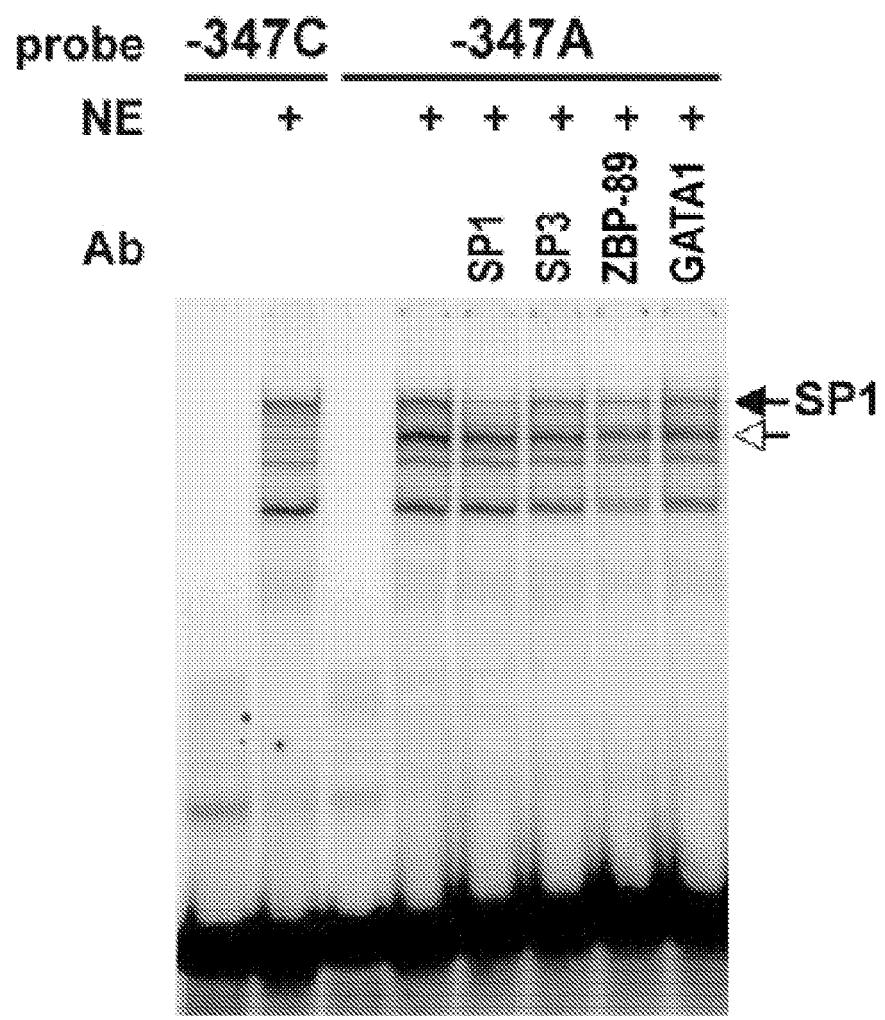
FIG. 5. Allele-specific binding of EGR-1 to the −347C/A polymorphism in the TPH1 core promoter. EMSA analysis using nuclear extract (NE*) from BON cells stimulated with TPA (1 h, 200 nM). Binding reactions were performed with allele-specific probes (−347C and −347A) and included antibodies (Ab) against SP1, SP3, ZBP-89, or GATA1.

In this example, the human TPH1 promoter was analyzed for ZBP-89 consensus regulatory elements. Several putative sites were identified in the proximal promoter with one near a biallelic SNP (at position −347 relative to the transcription start site). Therefore, EMSA was used to evaluate binding of nuclear proteins to sequences comprising the −347C/A SNP of the TPH1 promoter. Nuclear proteins were extracted from BON cells, a 5-HT producing human pancreatic carcinoid cell line. It was found that EMSA probes for either the C- or A-allele at −347 were specifically bound by three protein complexes (FIG. 1A). In addition, the EMSA revealed a distinct protein complex that preferentially bound to the −347A probe. Since the DNA element containing the SNP was flanked by a GC-rich element, it was tested whether zinc finger transcription factors accounted for differential binding of the protein complexes to the A-allele. Sp1 and to a lesser extent ZBP-89 decreased the intensity of the upper and lower complexes respectively, while there appeared to be little effect of the Sp3 and GATA1 antibodies (FIG. 1A and FIG. 5). However, none of these factors accounted for the novel complex binding preferentially to the A-allele. Therefore, it was examined whether DNA binding was induced by common signaling pathways, e.g., PKA activated by forskolin or PKC activated by phorbol esters. It was found that the allele-specific binding activity was robustly induced in serum-starved BON cells treated for one hour with FBS or TPA, but not by FSK (FIG. 1B).

Early Growth Response Factor 1 Binds Differentially to the TPH1 −347 SNP Site

Since rapid induction by FBS and TPA is a characteristic feature of immediate early genes, the possibility was considered that the novel protein binding to the −347A site would be an immediate-early transcription factor that recognizes GC-rich sequences. Few zinc finger transcription factors are known to rapidly increase their binding in response to proliferative signals. However, members of the EGR family of transcription factors are known to meet these criteria. Therefore, antibodies to EGR-1 and -3 were used to determine the identity of the allele-specific binding activity. Indeed, EGR-1 but not EGR-3 antibodies, completely shifted the A-allele-specific complex (FIG. 1C). It was demonstrated by Western blots that both TPA and FBS stimulate EGR-1 protein expression in BON cells (FIG. 1D). EGR-1 was robustly induced within one hour of stimulation, especially with TPA, consistent with increased binding on the EMSAs. Therefore the two alleles of the −347 TPH1 promoter SNP differentially bind EGR-1. When reviewed in silico, the extended weight matrix for EGR-1 binding sites, it was found that the SNP lies adjacent (position −1) to a nonameric EGR family recognition site overlapping an Sp1 recognition motif (FIG. 1E). In vitro DNA binding site selection studies indicate a strong preference for adenine at −1 of the extended EGR-1 binding matrix,[25] which is consistent with our EMSA results showing preferential binding of EGR-1 to the A-allele.

Promoter Activity of TPH1 −347C/A Alleles is Differentially Modulated by EGR-1

Figure 2:
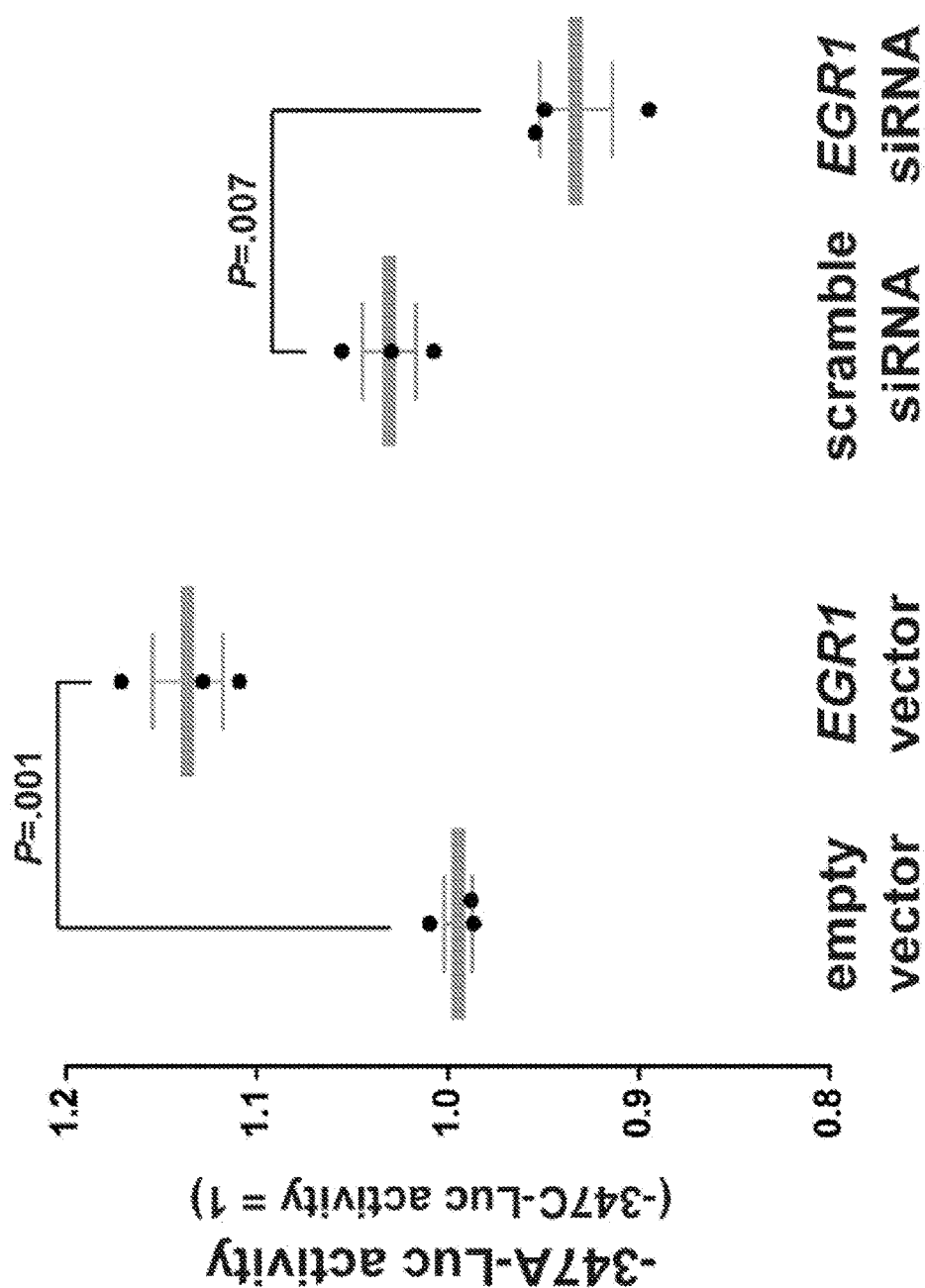
FIG. 2. Allele-specific activity of the TPH1(−568/+19) proximal promoter comprising either the C- or A-allele at position −347. Allele-specific luciferase reporter constructs were co-transfected with empty expression plasmid, EGR-1 encoding expression vector, scrambled control siRNA, or EGR1-specific siRNA followed by stimulation with 200 nM of TPA for 4 h. A co-transfected Renilla luciferase vector served as internal control for normalization. Data are from three independent experiments each performed in triplicate transfections and represent the relative activity of the A-allele (as fraction of the C-allele activity).

Having established that the common −347C/A SNP in the TPH1 promoter alters an EGR1 binding site, it was next examined whether differential binding of EGR-1 modulated TPH1 promoter activity. The human TPH1(−568/+19) proximal promoter region containing either the C or A-alleles was subcloned into a luciferase reporter plasmid and transfected into BON cells. To compare the relative activity of the two alleles under different conditions, the activity of the A-allele was expressed relative to the C-allele. The two SNP alleles did not cause differential reporter gene expression in cells cultured in serum-free medium and transfected with an insert-less control plasmid (A- to C-allele ratio ~1; FIG. 2). However, overexpression of EGR-1 resulted in higher relative expression of the A-allele. To further demonstrate differential modulation of the −347 SNP alleles by EGR-1, BON cells were transfected for 48 h with either pooled siRNA oligonucleotides against EGR1 or scrambled control siRNA followed by stimulation with TPA to activate EGR-1. Relative to the C-allele, the A-allele lost activity in cells transfected with EGR1 siRNA but not control siRNA (FIG. 2). Thus, these results indicate that the A-allele but not the C-allele is strongly regulated by EGR-1. In this way, the common −347C/A variant modulates the function of a bona fide cis-regulatory element. However since in vitro assays might not fully replicate the functional impact of the −347 variant in vivo, the prevalence of the two alleles was examined in patients with IBS, a disorder ostensibly correlated with TPH1 expression and 5-HT signaling.

Genetic Association of the −347C/A TPH1 Variant with IBS Bowel Habit Subtype

To test whether the functional −347C/A TPH1 promoter variant is associated with distinct bowel habit subtypes in IBS, 219 IBS patients (classified by their predominant bowel habit phenotype according to Rome III criteria) and 312 healthy controls were genotyped. Pertinent demographic and clinical characteristics of IBS and control groups are presented in Table 1.

TABLE 1

Clinical Characteristics of Subjects Included in the Genetic Study

| | Controls (n = 312) | IBS (n = 219) | P value |
|---|---|---|---|
| Female n (%) | 232 (74%) | 162 (74%) | .92 |
| Age (mean ± SEM) | 30.53 ± 0.61 | 37.16 ± 0.85 | .001 |
| BMI (mean ± SEM) | 24.3 ± 0.26 | 25.24 ± 0.38 | .05 |
| Race/Ethnicity n (%) | | | .001 |
| Caucasian | 112 (36%) | 124 (57%) | |
| Hispanic | 61 (20%) | 29 (13%) | |
| Asian | 79 (25%) | 20 (9%) | |
| African American | 41 (13%) | 27 (12%) | |
| Other/Multiracial | 17 (5%) | 16 (7%) | |
| HAD Scores (0-21) | | | |
| Anxiety | 3.27 ± 0.15 | 7.22 ± 0.28 | .001 |
| Depression | 1.22 ± 0.09 | 3.92 ± 0.23 | .001 |
| IBS Symptoms | | | |
| Overall Severity | — | 10.31 ± 0.31) | |
| Bowel Habit Subtype n (%) | | | |
| IBS-C | — | 43 (20%) | |
| IBS-D | — | 43 (20%) | |

TABLE 1-continued

Clinical Characteristics of Subjects Included in the Genetic Study

|  | Controls (n = 312) | IBS (n = 219) | P value |
|---|---|---|---|
| IBS-M | — | 124 (57%) |  |
| IBS-U | — | 9 (3%) |  |

IBS-C: constipation-predominant;
IBS-D: diarrhea-predominant;
IBS-M: mixed pattern;
IBS-U: unspecified subtype;
BMI: body mass index;
HAD: Hospital Anxiety and Depression Scale In the total sample, IBS patients were older and had significantly higher anxiety and depression symptom scores than controls although most were within normal range.

No significant departure from Hardy-Weinberg equilibrium was found for the −347C/A SNP (P>0.05). Also, genotype frequencies did not differ between IBS patients and controls overall or within any of the race/ethnic groups (FIG. 3) indicating that the −347C/A SNP was not a risk factor for IBS.

Figure 3:
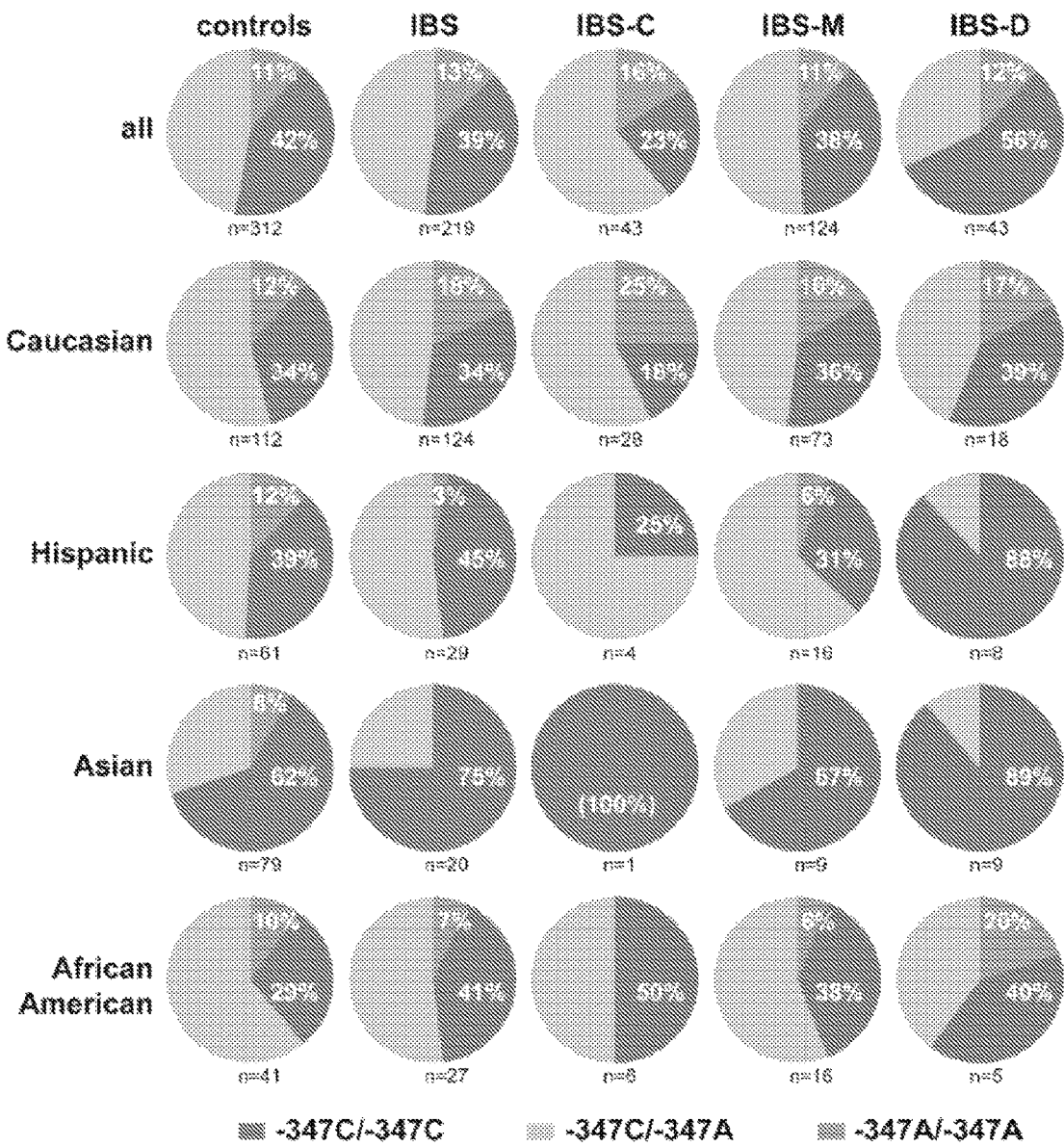
FIG. 3. Genotype frequency distribution of the −347C/A TPH1 polymorphism in healthy controls and IBS patients and within IBS bowel habit subtypes defined by Rome III criteria. Distribution of genotype frequencies with respect to race and ethnicity are also shown.

There was a significantly greater prevalence of the CC genotype in the IBS-D subtype (56%) compared to the IBS-C (31%) and IBS-M (38%) subtypes (P=0.030, FIG. 3). These differences in bowel habit remained significant in a multinomial regression model predicting bowel habit from additively coded TPH1 genotypes controlling for race/ethnicity and anxiety (P=0.050). In Caucasians, the largest racial group within the study population, the C-allele was more prevalent in the IBS-D vs. other bowel habit subtypes after controlling for anxiety (P=0.070). The odds ratio for comparing the prevalence of the C-allele in IBS-D to IBS-C was 2.3 (95% CI 0.92-5.74). Overall, these results indicate that the −347C/A polymorphism in the proximal TPH1 promoter is associated with bowel habit predominance within the IBS population.

To provide additional evidence that the functional −347C/A variant may play a causative role in the observed association with bowel habit in IBS, the haplotype structure of TPH1 was reviewed using genotype data for different racial and ethnic populations from the HapMap project. It was found that SNPs within TPH1 were only weakly correlated with those in the 5' upstream region, such as, −347C/A ($r^2$<0.6), indicating that the 5' upstream variants reside on a distinct haplotype block. To screen for the presence of other variants in strong linkage disequilibrium with −347C/A in the population that may contribute to the observed association, the extended TPH1 promoter region was sequenced up to position −1292. This identified one additional SNP (−1066T/C; rs4537731) but no other rare variants in the racially and ethnically diverse population. The genotypes for the two SNPs at −347 and −1066 were highly correlated ($r^2$~1) except for the African-American subpopulation ($r^2$~0.45) in which three common two-marker haplotypes were observed as shown in Table 3.

TABLE 3

Distribution of genotypes for the two common TPH1 promoter variants (−347C/A; −1066T/C), their correlation and estimated two-marker haplotype frequencies in a population of IBS patients (n = 158) and controls (n = 281)

|  | n | −347 (rs7130929) C/C | C/A | A/A | −1066 (rs4537731) T/T | T/C | C/C | haplotype frequencies f(−347/−1066)** f(CT) | f(AC) | f(CC) | f(AT) | $r^2$ (−347/−1066) |
|---|---|---|---|---|---|---|---|---|---|---|---|---|
| all ethnicities |  |  |  |  |  |  |  |  |  |  |  |  |
| Controls | 281 | 120 | 129 | 32 | 110 | 132 | 30 | 0.0626 | 0.343 | 0.030 | 0.000 | 0.877 |
| IBS | 158 | 67 | 70 | 21 | 60 | 70 | 28 | 0.601 | 0.354 | 0.044 | 0.000 | 0.828 |
| P* |  |  | 0.742 |  |  | 0.469 |  | 0.611 | 0.917 | 0.418 |  |  |
| Caucasian |  |  |  |  |  |  |  |  |  |  |  |  |
| Controls | 100 | 38 | 83 | 12 | 38 | 53 | 12 | 0.621 | 0.379 | 0.050 | 0.000 | 1.000 |
| IBS | 98 | 36 | 44 | 18 | 36 | 42 | 20 | 0.582 | 0.408 | 0.010 | 0.000 | 0.959 |
| P* |  |  | 0.477 |  |  | 0.364 |  | 0.611 | 0.886 | 0.495 |  |  |
| Hispanic |  |  |  |  |  |  |  |  |  |  |  |  |
| Controls | 57 | 22 | 28 | 7 | 21 | 28 | 8 | 0.614 | 0.377 | 0.009 | 0.000 | 0.964 |
| IBS | 18 | 8 | 9 | 1 | 8 | 9 | 1 | 0.694 | 0.306 | 0.050 | 0.000 | 1.000 |
| P* |  |  | 0.473 |  |  | 0.367 |  | 0.675 | 0.773 | 1.000 |  |  |
| Asian |  |  |  |  |  |  |  |  |  |  |  |  |
| Controls | 98 | 46 | 17 | 6 | 46 | 17 | 6 | 0.787 | 0.213 | 0.050 | 0.000 | 1.000 |
| IBS | 16 | 13 | 3 | 0 | 13 | 3 | 0 | 0.906 | 0.094 | 0.000 | 0.000 | 1.000 |
| P* |  |  | 0.162 |  |  | 0.162 |  | 0.505 | 0.505 | — |  |  |

EMSA probes comprising either the C- or T-allele at position −1066 showed no specific binding of nuclear proteins from BON cells. These results further support the notion that the −347C/A TPH1 variant itself influenced the bowel habit phenotype in the cohort of IBS patients.

Association of the −347C/A TPH1 Variant with Colonic Mucosal TPH1 mRNA

TPH1 mRNA was measured in colonic biopsies obtained from 62 patients with IBS (15 IBS-D, 32 IBS-M, 14 IBS-C, 1 IBS-U) and 50 healthy controls (Table 4). Of these subjects, 48 (77%) IBS patients and 42 (84%) controls had TPH1 genotyping.

TABLE 4

Clinical Characteristics of Subjects Included in the TPH1 Expression Study

|  | Controls (n = 50) | IBS (n = 62) |  |
|---|---|---|---|
| Female n (%) | 24 (48%) | 35 (56%) | .40 |
| Age | 39.79 ± 1.77 | 40.52 ± 1.61 | .78 |
| BMI | 25.58 ± 0.60 | 26.53 ± 0.87 | .73 |
| Race/Ethnicity n (%) |  |  | .32 |
| Caucasian | 25 (50%) | 13 (21%) |  |
| Hispanic | 5 (10%) | 8 (13%) |  |
| Asian | 6 (12%) | 8 (13%) |  |
| African American | 12 (24%) | 25 (40%) |  |
| Other/Multiracial | 2 (4%) | 4 (6%) |  |
| HAD Scores (0-21) |  |  |  |
| Anxiety | 3.41 ± 0.39 | 7.25 ± 0.69 | .001 |
| Depression | 1.59 ± 0.39 | 4.15 ± 0.56 | .001 |
| GI Symptoms |  |  |  |
| Overall Severity | NA | 10.91 ± 0.59 |  |
| Bowel Habit Subtype n (%) |  |  |  |
| IBS-C | NA | 14 (23%) |  |
| IBS-D | NA | 15 (24%) |  |
| IBS-M | NA | 32 (52%) |  |
| IBS-U | NA | 1 (2%) |  |

Figure 4:
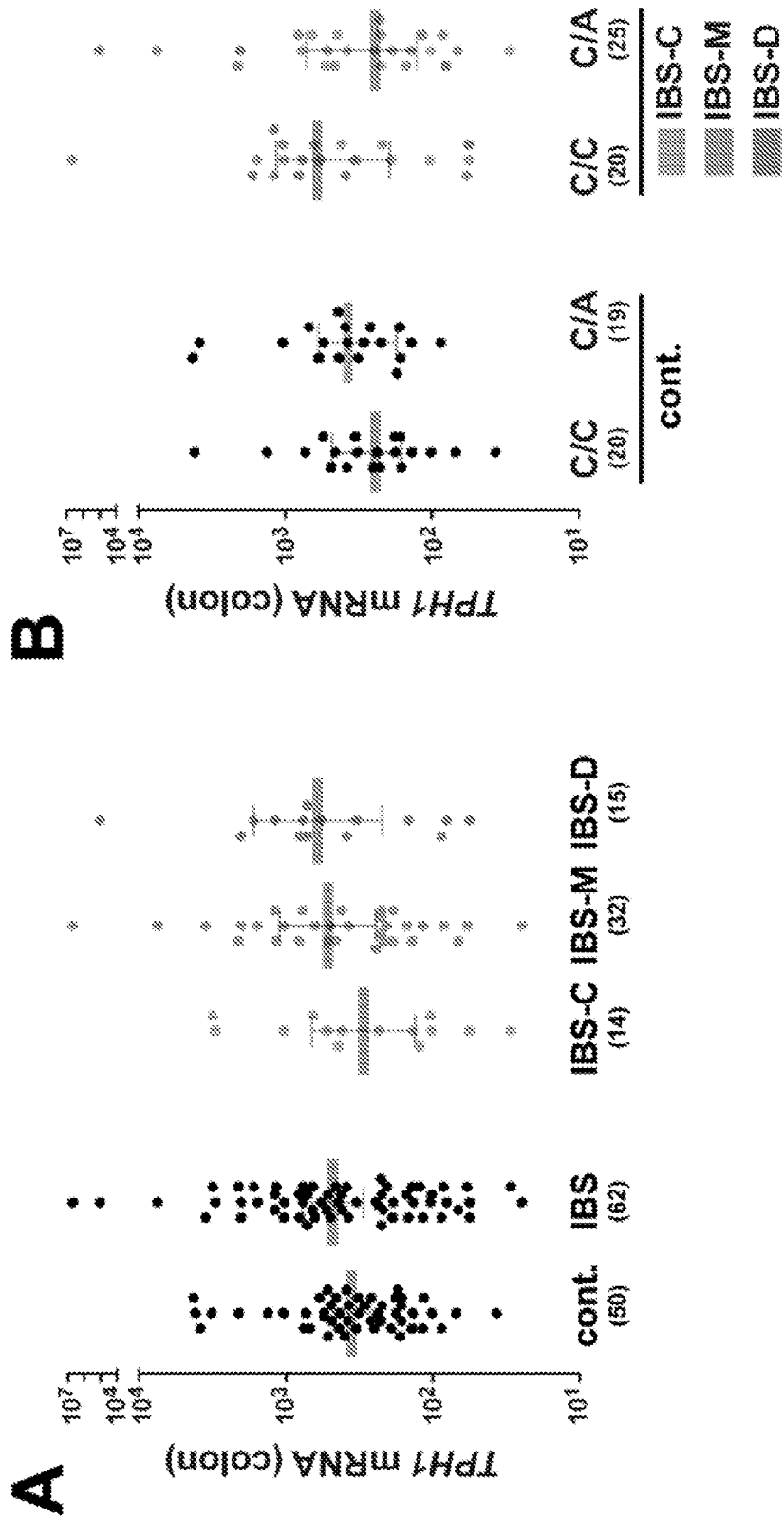
FIG. 4. Colonic expression of TPH1 mRNA in IBS patients. Relative TPH1 mRNA level was determined using real-time qRT-PCR normalized for the expression of 18S ribosomal RNA. Expression values followed a log-normal distribution (Kologorov-Smirnov test). Average and error bars correspond to the geometrical means±95% CI. (A) Expression of TPH1 in IBS bowel habit subtypes. (B) Segregation of TPH1 mRNA levels in controls and IBS patients with either −347C/−347C or −347C/−347A genotype. Note that only three subjects with −347A/−347A genotype were identified among the patients with colonic biopsies and genotype information (data not shown).

IBS-C: constipation-predominant;
IBS-D: diarrhea-predominant;
IBS-M: mixed pattern;
IBS-U: unspecified subtype;
BMI: body mass index;
HAD: Hospital Anxiety and Depression Scale TPH1 transcript levels tended to be higher in IBS-D patients (geometric mean [95% CI]; 610 [224-1664]) than in healthy control subjects (358 [267-481]; P=0.099) (FIG. 4A, and Table 5).

TABLE 5

TPH1 mRNA expression in colonic mucosal biopsies

|  | n | geometric mean | 95% CI |
|---|---|---|---|
| *All subjects with TPH1 mRNA levels* |  |  |  |
| Controls* | 50 | 358 | 267-481 |
| IBS* | 62 | 479 | 298-769 |
| IBS-C | 14 | 298 | 133-670 |
| IBS-M | 32 | 521 | 245-1108 |
| IBS-D | 15 | 610 | 224-1664 |
| *Subjects with TPH1 mRNA levels and TPH1 genotype* |  |  |  |
| Controls | 42 |  |  |
| −347C/−347C | 20 | 280 | 172-454 |
| −347C/−347A | 19 | 404 | 248-659 |
| −347A/−347A | 3 | 423 | 73-246 |
| IBS | 48 |  |  |
| −347C/−347C | 20 | 652 | 214-19 |
| −347C/−347A | 25 | 388 | 193-781 |
| −347A/−347A | 3 | 398 | 32-5009 |

*Eight controls and 14 IBS patients did not have TPH1 genotyping.
IBS-C: constipation-predominant;
IBS-D: diarrhea-predominant;
IBS-M: mixed pattern;
IBS-U: unspecified subtype In healthy controls, there was a non-significant trend for higher expression of TPH1 in heterozygotes (geometric mean [95% CI]; 404 [248-659]) compared to CC homozygotes (280 [172-454]; P=0.135; FIG. 4B, and Table 5), consistent with the in vitro promoter analysis showing enhanced expression of the A-allele after preferential binding of EGR-1. In contrast, among IBS patients, heterozygotes (388 [193-781]) appeared to have lower TPH1 mRNA expression compared to CC homozygotes (652 [214-1990]). An explanation is the possibility of higher EGR-1 promoter binding in unaffected controls but lower EGR-1 levels binding in IBS-affected individuals. Nevertheless, these results may be confounded by the predominance of IBS-D patients that were homozygous for the −347C allele (8 C/C vs 3 A/C among IBS-D patients with colonic biopsies and genotype information) (FIG. 4B), consistent with the association of the C-allele with the IBS-D subtype. Still, a trend towards higher TPH1 mRNA level in C-allele homozygotes was also observed in patients with IBS-M, the most predominant bowel habit subtype in this study (1402 [76-26029] for C/C vs 330[179-609] C/A; P=0.141). Segregation of the C-allele with higher TPH1 mRNA expression in IBS patients would be consistent with the genetic association of the C-allele with the IBS-D subtype and the notion of higher 5-HT bioavailability in IBS-D.

Discussion

In this Example, a functional variant in the human TPH1 promoter was identified that correlates with bowel habit subtype in IBS patients and also tends to be associated with TPH1 mRNA expression in colonic mucosal tissue. These results support the role of TPH1 as a candidate gene for conditions with abnormal mucosal 5-HT bioavailability as previously inferred from gene dosage effects in animal models.[15]

In the evaluation of sequences comprising the −347 SNP site for binding to nuclear proteins, it was found that EGR-1 preferentially bound to the A-allele sequence. This finding is consistent with in vitro binding site selection studies showing that the −1 position adjacent to the canonical EGR consensus sequence impacts the affinity of EGR-1 binding.[25] EGR-1 is an important mediator of a broad range of biological responses to environmental challenges. As an immediate early gene, EGR-1 is characterized by robust induction and therefore is well-suited to affect changes in mucosal TPH1 expression in response to psychological and luminal stressors. In intestinal epithelial cells, EGR-1 is a crucial activator of both injury-induced gene expression[26] and the acute response to water immersion-restraint stress in rats before the manifestation of mucosal injury.[27] Mucosal EGR-1 expression is also induced during chronic inflammation,[28] by infectious agents, such as, *Salmonella Typhimurium*[29] and enteropathogenic *E. coli*,[30] by a diet enriched in fermentable material,[31] and in response to feeding.[32] All these environmental challenges, as well as psychological stressors implicated as triggers for IBS symptoms, could conceivably exacerbate allelic expression imbalance secondary to the polymorphism at −347C/A.

Although EGR-1 is considered an activating transcription factor, the effect of differential EGR-1 binding to the −347C/A SNP site is likely more complex. The EGR-1 binding site overlaps a recognition motif for Sp1 indicating potential competition of both factors for DNA binding as shown for other overlapping EGR-1/Sp1 binding motifs.[33-38] The relative levels of both EGR-1 and Sp1 are therefore expected to modulate the activity of the −347A-allele, which could be relatively higher (EGR-1 activator effect predominant) or lower (displacement of bound Sp1 predominant) compared to the −347C-allele. In BON cells, an isolated proximal promoter fragment harboring the A-allele showed more robust expression compared to the C-allele only in the presence of EGR-1, indicating that under these experimental conditions, transactivation by promoter-bound EGR-1 is the predominant effect. In agreement with the in vitro data, colonic expression of TPH1 appeared to be higher in healthy subjects carrying an A-allele (−347C/−347A heterozygotes) compared to C-allele homozygotes (FIG. 4B). In contrast, a suppressive effect of EGR-1 on the A-allele would be more congruent with the findings in IBS patients, showing an association of the C-allele with IBS-D and a trend toward higher colonic TPH1 mRNA expression in C-allele homozygotes compared to heterozygotes. Alternatively signals inducing IBS symptoms might reduce EGR-1 promoter binding in subjects with the A-allele favoring lower TPH1 mRNA and 5-HT levels.

The one method to further elucidate the impact of differential EGR-1 binding on TPH1 expression in vivo would be the analysis of allele-specific TPH1 transcription in heterozygous individuals. Unfortunately, since the TPH1 promoter region lies on a haplotype block separate from the remaining gene structure,[39,40] there are no common variants on the TPH1 mRNA in sufficient correlation ($r^2>0.8$) with the promoter SNP that could be used as reasonable proxy for −347C/A in allele-specific expression analysis.

While intragenic TPH1 SNPs form a distinct haplotype block from the −347C/A SNP, other common SNPs in the 5' upstream region of TPH1 are highly correlated with −347C/A (Table 3). One study reported that for a three marker haplotype comprising the SNPs at position −347C/A (rs7130929), −1066T/C (rs4537731), and −1605G/A (rs4757610), the minor A-C-A haplotype had a pronounced loss of basal activity compared to the C-T-G haplotype in reporter assays.[41] This Example tested 1857 bp of the extended promoter region [−1838/+19] that represented either the major C-T-G, the minor A-C-A, or the African-specific C-C-G haplotype and did not observe lower basal activity of the A-C-A haplotype in BON cells (data not shown). The reason for the discrepancy with the previous study is unclear, but could be related to the use of different cell types.

The −347C/A variant was not directly associated with the diagnosis of IBS. This finding is consistent with the results of a recent study by Jun et al. in Caucasian female IBS patients and healthy controls showing that the −1066T/C promoter variant, which is linked to the −347C/A genotype in this racial group (Table 3), does not predict IBS susceptibility.[40] Rather, the promoter SNP predicts bowel habit predominance. However, Jun et al. found that patients who were homozygous for the minor allele of the −1066T/C promoter variant had a higher severity of daily diarrhea symptoms compared to the other two genotypes but there were no differences in bowel habit subtype. This differs from this Example, which showed that patients who were homozygous for the major allele of the −347 SNP were more likely to have IBS-D vs. IBS-C. This Example did not measure daily IBS symptoms. Of note, a similar bowel habit subtype association of IBS-D was found with the major allele of −1066T/C promoter variant in the IBS patient population (data not shown).

The association of a functional promoter variant in TPH1, encoding the rate-limiting enzyme for intestinal mucosal 5-HT synthesis, with distinct bowel habit subtypes in IBS suggests a causative relationship. Hence, differential gene expression of TPH1 was predicted in IBS patients according to subtype (IBS-D>IBS-C) and −347C/A genotype (C-allele >A-allele). It was found that colonic mucosal expression of TPH1 tended to be higher in IBS-D patients compared to IBS-C and in the IBS patients who were homozygous for the C-allele. This Example suggests that TPH1 mRNA levels are dependent on the TPH1 genotype but its influence on bowel habit symptoms is likely modified by other factors (e.g., SERT, 5-HT receptor expression).

In summary, word conducted during the development of the present invention has identified a proximal TPH1 promoter SNP that segregates with stool consistency (bowel habit predominance) in a racially and ethnically diverse patient population with IBS. This variant differentially affects binding of the transcription factor EGR-1, an early response gene product that is sufficient to modulate TPH1 gene expression. As a result, the SNP was predictive of TPH1 mRNA levels in vivo and could play a valuable role in predicting an IBS patient's response to a serotonergic therapy. In addition, this Example suggests that distinct IBS bowel habit subtypes can be affected by racial or ethnic background and is associated with other genetic factors in 5-HT pathway genes.

Example 2

This Example describes genotyping in Crohn's disease (CD) patients. Symptoms resembling IBS are frequently found in patients with Crohn's disease in remission. Those patients were found to have higher Tph1 levels in the colon compared to CD patients in remission without IBS-like symptoms and to healthy controls (Minderhoud et al., Clin Gastroenterol Hepatol. 2007 June; 5(6):714-20).

The results shown in Table 6 demonstrate association of CD with the A allele at −347. SNP −347 C/A is therefore useful in the stratification of CD patients for anti-serotonergic treatment.

TABLE 6

| rs7130929 (C/A) | | | | | |
|---|---|---|---|---|---|
| | n (chr) | A/A | A/C | C/C | A | C |
| CD (Cho) | 100 | 0.320 | 0.440 | 0.240 | 0.540 | 0.460 |
| HapMap (CEU | 118 | 0.186 | 0.508 | 0.305 | 0.441 | 0.559 |
| HapMap (YRI) | 120 | 0.167 | 0.517 | 0.317 | 0.425 | 0.575 |
| UC (Cho) | 100 | 0.140 | 0.400 | 0.460 | 0.340 | 0.660 |
| N-white (Chang) | 294 | 0.120 | 0.480 | 0.410 | 0.354 | 0.646 |
| N-all (Chang) | 610 | 0.110 | 0.470 | 0.420 | 0.348 | 0.652 |
| HapMap (HCB) | 88 | 0.068 | 0.364 | 0.568 | 0.250 | 0.750 |
| SUNLAB (Chinese) | 388 | 0.005 | 0.433 | 0.562 | 0.222 | 0.778 |
| HapMap (JPT) | 88 | 0.023 | 0.386 | 0.591 | 0.216 | 0.784 |

| | A/A | A/C | C/C | n (cases) | HWE |
|---|---|---|---|---|---|
| CD | 16 | 22 | 12 | 50 | y |
| HapMap (CEU) | 11 | 30 | 18 | 59 | y |
| UC | 7 | 20 | 23 | 50 | y |
| N-all (Chang) | 34 | 144 | 127 | 305 | y |
| CD vs N-all | A = risk allele | | | | |
| | | OR | 95% CI | | p |
| AA vs CC | | 4.98 | 2.15-11.52 | | 7E−05 |
| AA/ac vs CC | | 2.26 | 1.14-4.5 | | 0.0179 |
| ac vs CC | | 1.617 | 0.77-3.4 | | 0.2 |
| Cochran-Armitage's trend: | | | | | |
| | | common OR | | | |
| | | 2.21 | | | 0.0002 |

REFERENCES

1. Gershon M D, Tack J. The serotonin signaling system: From basic understanding to drug development for functional GI disorders. Gastroenterology 2007; 132:397-414

2. Bearcroft C P, Perrett D, Farthing M J. Postprandial plasma 5-hydroxytryptamine in diarrhoea predominant irritable bowel syndrome: A pilot study. Gut 1998; 42:42-46

3. Atkinson W, Lockhart S, Whorwell P J, et al. Altered 5-hydroxytryptamine signaling in patients with constipation- and diarrhea-predominant irritable bowel syndrome. Gastroenterology 2006; 130:34-43

4. Houghton L A, Atkinson W, Whitaker R P, et al. Increased platelet depleted plasma 5-hydroxytryptamine concentration following meal ingestion in symptomatic female subjects with diarrhoea predominant irritable bowel syndrome. Gut 2003; 52:663-670

5. Zuo X L, Li Y Q, Yang X Z, et al. Plasma and gastric mucosal 5-hydroxytryptamine concentrations following cold water intake in patients with diarrhea-predominant irritable bowel syndrome. J Gastroenterol Hepatol 2007; 22:2330-2337

6. Dunlop S P, Coleman N S, Blackshaw E, et al. Abnormalities of 5-hydroxytryptamine metabolism in irritable bowel syndrome. Clin Gastroenterol Hepatol 2005; 3:349-357

7. Houghton L A, Atkinson W, Lockhart C, et al. Sigmoid-colonic motility in health and irritable bowel syndrome: A role for 5-hydroxytryptamine. Neurogastroenterol Motil 2007; 19:724-731

8. Ford A C, Talley N J, Schoenfeld P S, et al. Efficacy of antidepressants and psychological therapies in irritable bowel syndrome: Systematic review and meta-analysis. Gut 2009; 58:367-378

9. Coates M D, Mahoney C R, Linden D R, et al. Molecular defects in mucosal serotonin content and decreased serotonin reuptake transporter in ulcerative colitis and irritable bowel syndrome. Gastroenterology 2004; 126:1657-1664

10. Camilleri M, Andrews C N, Bharucha A E, et al. Alterations in expression of p11 and SERT in mucosal biopsy specimens of patients with irritable bowel syndrome. Gastroenterology 2007; 132:17-25

11. Kerckhoffs A P, Ter Linde J J, Akkermans L M, et al. Trypsinogen iv, serotonin transporter transcript levels and serotonin content are increased in small intestine of irritable bowel syndrome patients. Neurogastroenterol Motil 2008; 20:900-907

12. Spiller R, Bennett A. Searching for the answer to irritable bowel syndrome in the colonic mucosa: Sertainty and unsertainty. Gastroenterology 2007; 132:437-441

13. Li Z, Chalazonitis A, Huang Y Y, et al. Essential roles of enteric neuronal serotonin in gastrointestinal motility and the development/survival of enteric dopaminergic neurons. J Neurosci 2011; 31:8998-9009

14. Huang Z, Liu T, Chattoraj A, Ahmed S, et al. Posttranslational regulation of TPH1 is responsible for the nightly surge of 5-HT output in the rat pineal gland. J Pineal Res 2008; 45:506-514

15. Liu Q, Yang Q, Sun W, et al. Discovery and characterization of novel tryptophan hydroxylase inhibitors that selectively inhibit serotonin synthesis in the gastrointestinal tract. J Pharmacol Exp Ther 2008; 325:47-55

16. Brown P M, Drossman D A, Wood A J, et al. The tryptophan hydroxylase inhibitor LX1031 shows clinical benefit in patients with nonconstipating irritable bowel syndrome. Gastroenterology 2011; 141:507-516

17. Tack J, Janssen P, Wouters M, et al. Targeting serotonin synthesis to treat irritable bowel syndrome. Gastroenterology 2011; 141:420-422

18. Camilleri M. LX-1031, a tryptophan 5-hydroxylase inhibitor, and its potential in chronic diarrhea associated with increased serotonin. Neurogastroenterol Motil 2011; 23:193-200

19. Longstreth G F, Thompson W G, Chey W D, et al. Functional bowel disorders. Gastroenterology 2006; 130: 1480-1491

20. Zigmond A S, Snaith R P. The hospital anxiety and depression scale. Acta Psychiatr Scand 1983; 67:361-370

21. Boularand S, Darmon M C, Mallet J. The human tryptophan hydroxylase gene. An unusual splicing complexity in the 5'-untranslated region. J Biol Chem 1995; 270:3748-3756

22. Parekh D, Ishizuka J, Townsend C M, Jr., et al. Characterization of a human pancreatic carcinoid in vitro: Morphology, amine and peptide storage, and secretion. Pancreas 1994; 9:83-90

23. Schreiber E, Matthias P, Muller M M, et al. Rapid detection of octamer binding proteins with 'mini-extracts', prepared from a small number of cells. Nucleic Acids Res 1989; 17:6419

24. Merchant J L, Iyer G R, Taylor B R, et al. Zbp-89, a kruppel-like zinc finger protein, inhibits epidermal growth factor induction of the gastrin promoter. Mol Cell Biol 1996; 16:6644-6653

25. Swirnoff A H, Milbrandt J. DNA-binding specificity of ngfi-a and related zinc finger transcription factors. Mol Cell Biol 1995; 15:2275-2287

26. Dieckgraefe B K, Weems D M. Epithelial injury induces egr-1 and fos expression by a pathway involving protein kinase C and ERK. Am J Physiol 1999; 276:G322-G330

27. Ueyama T, Saika M, Koreeda C, et al. Water immersion-restraint stress induces expression of immediate-early genes in gastrointestinal tract of rats. Am J Physiol 1998; 275:G287-G295

28. Subbaramaiah K, Yoshimatsu K, Scherl E, et al. Microsomal prostaglandin E synthase-1 is overexpressed in inflammatory bowel disease. Evidence for involvement of the transcription factor Egr-1. J Biol Chem 2004; 279:12647-12658

29. Bruno V M, Hannemann S, Lara-Tejero M, et al. *Salmonella typhimurium* type III secretion effectors stimulate innate immune responses in cultured epithelial cells. PLoS Pathog 2009; 5:e1000538

30. De Grado M, Rosenberger C M, Gauthier A, et al. Enteropathogenic *Escherichia coli* infection induces expression of the early growth response factor by activating mitogen-activated protein kinase cascades in epithelial cells. Infect Immun 2001; 69:6217-6224

31. Chen Q, Swist E, Beckstead J, et al. Dietary fructooligosaccharides and wheat bran elicit specific and dose-dependent gene expression profiles in the proximal colon epithelia of healthy Fischer 344 rats. J Nutr 2011; 141: 790-797

32. Holt P R, DuBois R N, Jr. In vivo immediate early gene expression induced in intestinal and colonic mucosa by feeding. FEBS Lett 1991; 287:102-104

33. Fukada T, Tonks N K. The reciprocal role of Egr-1 and Sp family proteins in regulation of the PTP1B promoter in response to the p210 Bcr-Abl oncoprotein-tyrosine kinase. J Biol Chem 2001; 276:25512-25519

34. Raychowdhury R, Schafer G, Fleming J, et al. Interaction of early growth response protein 1 (Egr-1), specificity protein 1 (Sp1), and cyclic adenosine 3'5'-monophosphate response element binding protein (CREB) at a proximal response element is critical for gastrin-dependent activation of the chromogranin a promoter. Mol Endocrinol 2002; 16:2802-2818
35. Bahouth S W, Beauchamp M J, Vu K N. Reciprocal regulation of beta(1)-adrenergic receptor gene transcription by Sp1 and early growth response gene 1: Induction of EGR-1 inhibits the expression of the beta(1)-adrenergic receptor gene. Mol Pharmacol 2002; 61:379-390
36. Davis W, Jr., Chen Z J, Ile K E, et al. Reciprocal regulation of expression of the human adenosine 5'-triphosphate binding cassette, sub-family A, transporter 2 (ABCA2) promoter by the early growth response-1 (EGR-1) and Sp-family transcription factors. Nucleic Acids Res 2003; 31:1097-1107
37. Li X, Nie S, Chang C, Qiu T, et al. Smads oppose Hox transcriptional activities. Exp Cell Res 2006; 312:854-864
38. Kubosaki A, Tomaru Y, Tagami M, et al. Genome-wide investigation of in vivo EGR-1 binding sites in monocytic differentiation. Genome Biol 2009; 10:R41
39. Lai T J, Wu C Y, Tsai H W, et al. Polymorphism screening and haplotype analysis of the tryptophan hydroxylase gene (TPH1) and association with bipolar affective disorder in Taiwan. BMC Med Genet 2005; 6:14
40. Jun S, Kohen R, Cain K C, et al. Associations of tryptophan hydroxylase gene polymorphisms with irritable bowel syndrome. Neurogastroenterol Motil 2011; 23:233-239, e116
41. Sun H S, Fann C S, Lane H Y, et al. A functional polymorphism in the promoter region of the tryptophan hydroxylase gene is associated with alcohol dependence in one aboriginal group in Taiwan. Alcohol Clin Exp Res 2005; 29:1-7
42. Schneider T D, Stephens R M. Sequence logos: A new way to display consensus sequences. Nucleic Acids Res 1990; 18:6097-6100
43. Gaunt T R, Rodriguez S, Day I N. Cubic exact solutions for the estimation of pairwise haplotype frequencies: Implications for linkage disequilibrium analyses and a web tool 'cubex'. BMC Bioinformatics 2007; 8:428

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating comprising:
   a) obtaining a sample from a human subject;
   b) detecting a homozygous polymorphism selected from rs7130929 allele C, rs4537731 allele T, and rs4757610 allele G, in the sample,
   c) diagnosing the subject with diarrhea-predominant irritable bowel syndrome (IBS-D) when said homozygous polymorphism is detected in the sample; and
   d) treating said subject with an effective amount of a serotonin antagonist medication, wherein said serotonin antagonist medication targets TPH1.

2. The method of claim 1, wherein said medication is LX1031.

3. The method of claim 1, wherein said subject is identified as homozygous for rs7130929 allele C.

4. The method of claim 1, wherein said subject is identified as homozygous for rs4537731 allele T.

5. The method of claim 1, wherein the subject is administered a 5HT3 antagonist.

6. The method of claim 1, wherein the subject is further identified as having a haplotype comprising rs7130929 allele C, rs4537731 allele T, and rs4757610 allele G.

* * * * *